US012642615B2

(12) United States Patent
Tan et al.

(10) Patent No.: US 12,642,615 B2
(45) Date of Patent: Jun. 2, 2026

(54) PANEL CONVEYANCE APPARATUS AND PANEL CONVEYANCE METHOD

(71) Applicants: KAWASAKI JUKOGYO KABUSHIKI KAISHA, Kobe (JP); Kawasaki Robotics (USA), INC., Wixom, MI (US)

(72) Inventors: Haruhiko Tan, Kobe (JP); Hajime Nakahara, San Jose, CA (US); Mu-Kai Lin, Santa Clara, CA (US)

(73) Assignees: KAWASAKI JUKOGYO KABUSHIKI KAISHA, Kobe (JP); Kawasaki Robotics (USA), INC., Wixom, MI (US)

( * ) Notice: Subject to any disclaimer, the term of this patent is extended or adjusted under 35 U.S.C. 154(b) by 394 days.

(21) Appl. No.: 18/470,463

(22) Filed: Sep. 20, 2023

(65) Prior Publication Data

US 2025/0090257 A1     Mar. 20, 2025

(51) Int. Cl.
A61B 34/00          (2016.01)
A61B 34/30          (2016.01)

(52) U.S. Cl.
CPC ........ A61B 34/76 (2016.02); A61B 2034/305 (2016.02)

(58) Field of Classification Search
CPC ... A61B 34/76; H01L 21/68; H01L 21/67259; H01L 21/67796
See application file for complete search history.

(56) References Cited

U.S. PATENT DOCUMENTS

| | | | | |
|---|---|---|---|---|
| 5,917,601 A * | 6/1999 | Shimazaki | ............. | G01D 5/342 356/400 |
| 6,126,381 A * | 10/2000 | Bacchi | ............. | H01L 21/67766 414/754 |
| 7,039,501 B2 * | 5/2006 | Freeman | ................. | H01L 21/68 700/229 |
| 7,963,736 B2 * | 6/2011 | Takizawa | ............. | H01L 21/681 414/217 |

(Continued)

FOREIGN PATENT DOCUMENTS

| | | | | |
|---|---|---|---|---|
| CN | 1405839 A * | 3/2003 | ............. | H01L 21/68 |
| JP | 3955499 B2 | 8/2007 | | |

(Continued)

*Primary Examiner* — Patrick H Mackey
(74) *Attorney, Agent, or Firm* — METROLEX IP LAW GROUP, PLLC; Robert L. Scott, Esq.

(57)          ABSTRACT
A panel transfer device according to one or more embodiment may include a base; an arm rotatably connected to the base, which includes a first detector; an end effector connected to the arm, including: a connector rotatably connected to the arm; a wrist connected to the connector, including a second detector; and a pair of forks connected to the wrist, including sensors. In response to the end effector gripping the panel, the sensor detects displacement of the panel in a first direction, the end effector rotates to a position where the first and second detectors face each other, the first and second detectors communicate to detect displacement of the panel in a second direction, and the panel transfer device calculates a correction amount based on the detected displacement of the panel in the first direction and in the second direction, and places the panel based on the correction amount.

9 Claims, 11 Drawing Sheets

(56) References Cited

U.S. PATENT DOCUMENTS

| | | | |
|---|---|---|---|
| 11,745,354 B2 * | 9/2023 | Atherton | B25J 9/1664 |
| | | | 700/259 |
| 2013/0211571 A1 | 8/2013 | Teramoto et al. | |
| 2015/0045950 A1 | 2/2015 | Kobayashi | |
| 2020/0144409 A1 | 5/2020 | Thaulad et al. | |

FOREIGN PATENT DOCUMENTS

| | | | | |
|---|---|---|---|---|
| JP | 4395873 B2 | | 1/2010 | |
| JP | 4980127 B2 | | 7/2012 | |
| JP | 5702975 B2 | | 4/2015 | |
| JP | 6309220 B2 | | 4/2018 | |
| JP | 6923346 B2 | | 8/2021 | |
| JP | 2021-167042 A | | 10/2021 | |
| JP | 2021-167043 A | | 10/2021 | |
| JP | 2021-167044 A | | 10/2021 | |
| JP | 2021-167045 A | | 10/2021 | |
| JP | 2023-081078 A | | 6/2023 | |
| KR | 20070097913 A | * | 10/2007 | B65G 49/067 |
| TW | 559584 U | | 5/2018 | |
| TW | 202035260 A | | 10/2020 | |
| WO | WO-2005004227 A1 | * | 1/2005 | H01L 21/68707 |

* cited by examiner

PANEL CONVEYANCE APPARATUS AND PANEL CONVEYANCE METHOD

BACKGROUND

The present disclosure relates to a transfer device, and in particular to a transfer device and a method for transferring substrates and panels.

In manufacturing substrates such as semiconductor substrates and liquid crystal substrates, and various panels (hereinafter referred to as "panels" in general), multiple manufacturing devices are used. Panel transfer devices are used to transfer panels between these manufacturing devices. Transfer devices include industrial robots.

Japanese patent 3,955,499 (Yazawa) discloses a technique for positioning a robot hand by advancing it above or below a workpiece from the front-back direction. In Yazawa, the hand has a pair of first sensors arranged side-by-side in the left-right direction and a second sensor provided on the side. The hand is advanced above or below the above workpiece from the front and rear directions.

Next, the inclination angle θ of the above workpiece in the left or right direction is obtained based on the difference in the coordinates of the above robot at which the above pair of first sensors detect the front or rear edge of the above workpiece during the hand's entry. Next, the above hand is inclined in the left-right direction above or below the above workpiece by an inclination angle θ. Next, with the above hand inclined by the inclination angle θ in the left-right direction, the above hand is moved in the left-right direction until the above second sensor detects the side edge of the above workpiece. Next, with the above hand inclined by an inclination angle θ in the left-right direction, the above hand is moved in the direction inclined by an inclination angle θ from the front-back direction until the above pair of first sensors detect the front edge or rear edge of the above workpiece.

SUMMARY

A panel transfer device according to one or more embodiments may include: a base; an arm rotatably connected to the base, which comprises a sensor and a detector; an end effector connected to the arm, including: a connector rotatably connected to the arm; a wrist connected to the connector; and a pair of forks connected to the wrist, wherein the sensor detects displacement of the panel in the first direction at the end effector gripping the panel, the second detector emits light to detect the panel and receives the light reflected from the panel to detect displacement of the panel in the second direction, and the panel transfer device calculates a correction amount based on the detected displacement of the panel in the first direction and in the second direction, and places the panel based on the correction amount.

A panel transfer device according to one or more embodiments may include a panel transfer device comprising a base; an arm rotatably connected to the base and including a sensor and a first detector; an end effector connected to the arm comprising: a connecting part rotatably connected to the arm; a wrist part connected to the connecting part and including a second detector; and a pair of forks connected to the wrist part, wherein the end effector is rotatably connected to the arm. Connection freely connected to the arm; a wrist connected to the connection and including a second detector; and a pair of forks connected to the wrist, wherein in response to the end effector gripping a panel, the end effector is placed in a position where the first detector and the second detector are facing each other, and position wherein the sensor is capable of detecting the panel, the sensor detects the displacement of the panel in the first direction when the end effector grips the panel, the first detector and the second detector communicate to detect the displacement of the panel in the second direction, and the panel transfer calculates a correction amount based on the detected displacement of the panel in the first direction and in the second direction, and places the panel based on the correction amount.

A method of transferring a panel according to one or more embodiments may include: gripping a panel; detecting displacement of the panel in a first direction of the gripped panel; moving the gripped panel to a position; detecting displacement of the panel in the second direction; calculating correction amount on the detected displacement of the panel in the first and second directions; and placing the gripped panel based on the correction amount.

DETAILED DESCRIPTION

Figure 1:
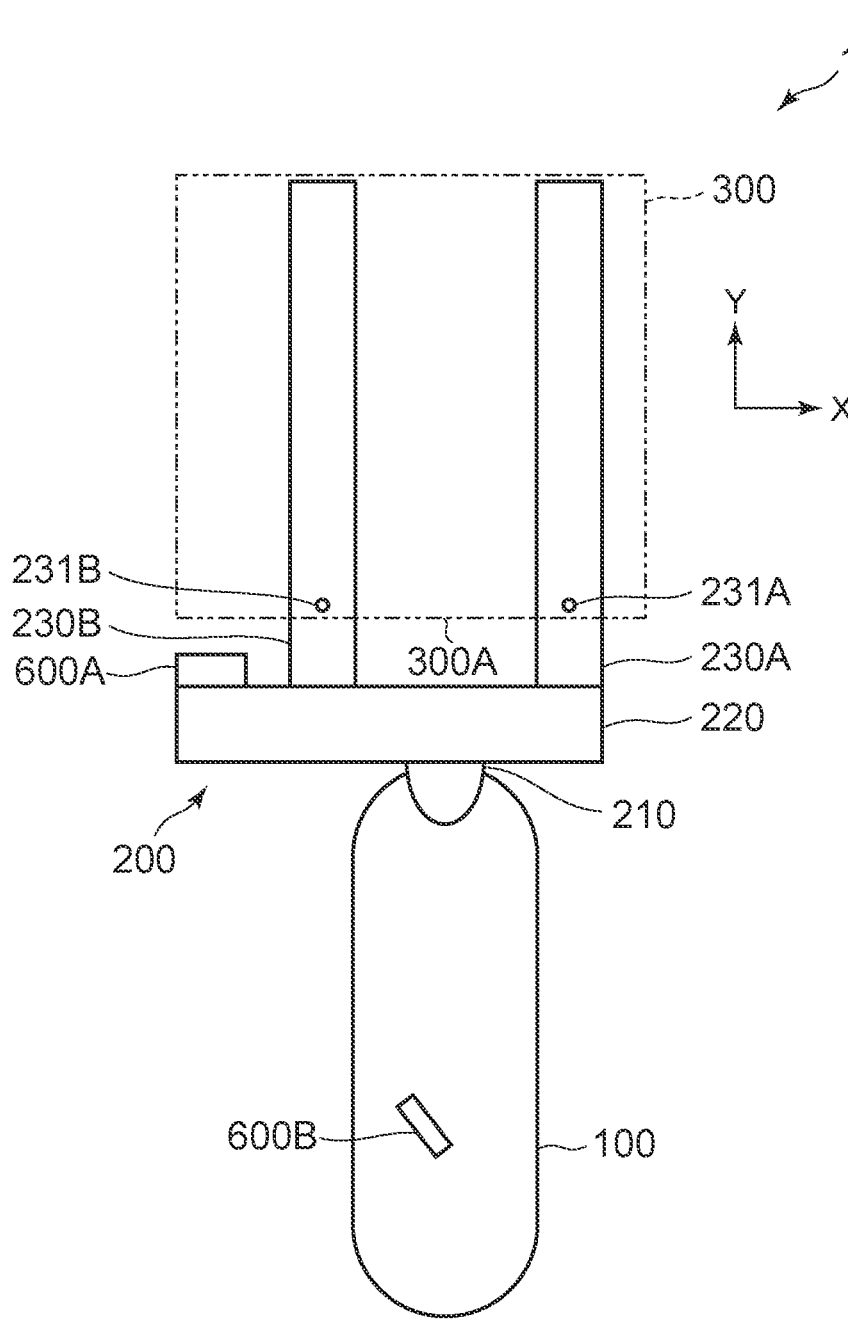
FIG. 1 is a diagram illustrating a top view of a panel transfer device according to one or more embodiments.

A panel transfer device and a panel transfer method according to one or more embodiments are described in detail with reference to the drawings. In the description of the drawings, the same or similar parts may be marked with the same or similar symbols. The descriptions in the drawings are schematic, and the relationship between thickness and dimensions, and the ratio of length, thickness, etc. of each part are examples, and do not limit the scope of the technical concept. The relationship between dimensions and the ratio of dimensions may differ among the drawings. In the following explanations, "above," "below," "right side," "left side," etc. are used as appropriate based on the orientation of the drawing referenced or the specific subject matter when describing the positional relationship of each component, but these indications do not limit the scope of the technical concept. Expressions such as "top," "bottom,"

"right side," and "left side" may be used even when the respective parts are not touched. The "length direction" may mean the direction of the long side on the main surface of the member. Width direction" may mean the direction of the short side of the main surface of the member. The "height direction" and "vertical direction" may mean the direction related to the thickness of the main surface of the member. The X-axis, Y-axis, Z-axis, or a combination thereof may be indicated in the figures, and "X-axis direction," "Y-axis direction," and "Z-axis direction" may be used in the specification or drawings to describe directions.

FIG. 1 is a diagram illustrating a panel transfer device 1 according to one or more embodiments. The panel transfer device 1 includes an arm 100 rotatably connected to a base (not shown) and an end effector 200 rotatably connected to the arm 100 and transferring a panel 300. The panel transfer device 1 shown in FIG. 1 is particularly, but not exclusively, a horizontally articulated panel transfer device. Various operations of the panel transfer device 1 are controlled by a controller (not shown). The controller controls the operation of the arm 100 and the end effector 200, including rotation of the end effector 200.

The end effector 200 is connected to one end of the arm 100 and the base is connected to the other end of the arm 100. The arm 100 may be solidly attached to the base. The arm 100 includes a receiver 600B. The panel transfer device 1 shown in FIG. 1 may not be limited to the arm 100 and the end effector 200. For example, a second arm may be provided that is rotatably connected to each of the arm 100 and the base. The end effector 200 may also be in the so-called linear motion type, where the end effector 200 is movably connected to the base.

The end effector 200 includes a connector 210 that rotatably connects to arm 100, a wrist 220 connected to connector 210, and a pair of forks 230A and 230B connected to wrist 220. The end effector 200, under the control of the controller, retrieves the panel 300 from a predetermined position using the forks 230A and 230B and transfers the panel 300 to the predetermined position. The fork 230A includes the sensor 231A. The fork 230B also includes the sensor 231B. When acquiring the panel 300 from a predetermined position, forks 230A and 230B are advanced above or below the panel 300, and the sensors 231A and 231B detect the front edge 300A of the panel 300 to be acquired. When the sensors 231A and 231B detect the front edge 300A of the panel 300 to be acquired, they recognize that the forks 230A and 230B have been advanced into position. When the forks 230A and 230B are recognized as having advanced the panel 300 to a predetermined position, the forks 230A and 230B stop advancing. The gripping operation of the panel 300 is then performed. After the forks 230A and 230B grip the panel 300, the sensors 231A and 231B detect the coordinates of the panel 300 respectively, and based on the difference of these detected coordinates, the vertical inclination angle of the panel 300 is detected. This detects the displacement of the panel 300 in the Y-axis direction, thereby performing the first position detection of the panel 300. The first position detection may be performed after the panel 300 is gripped, either with the panel 300 stopped immediately after the panel 300 is gripped, or with the panel 300 being transferred to a predetermined position. The connector 210, wrist 220, and forks 230A and 230B included in the end effector 200 may be formed in total or in part as one piece. The sensors 231A and 231B are located at the base of the pair of forks 230A and 230B, i.e., near the wrist 220, but not limited thereto. For example, the sensors 231A and 231B may be disposed at the tip portion of the pair of forks 230A and 230B to detect the rear end of the panel 300.

The operation of gripping the panel 300 by the forks 230A and 230B may use a vacuum suction type. For example, a suction unit (not shown) is provided on each of forks 230A and 230B, the suction unit is brought into proximity or contact with panel 300 from the top or bottom of the panel 300, and negative pressure is applied to the suction unit to cause the suction unit to be sucked onto the panel 300. This causes the end effector 200 to grip the panel 300 and transfer it to a predetermined position. Other gripping actions of the panel 300 may include the passive gripping method. The first position detection may be performed when the panel 300 is gripped using the forks 230A and 230B. The end effector 200 includes an emitter 600A. The emitter 600A, together with the receiver 600B included in arm 100, performs position detection of the gripped panel 300.

The panel 300 includes substrates such as semiconductor substrates, liquid crystal substrates, and various other panels. For example, the panel shown in FIG. 1 is a rectangle, but it is not limited to this and may be triangular, pentagonal, or hexagonal. It may also be circular. The panel 300 may be a transparent material including a material that transmits light, or it may be translucent or non-transparent.

Figure 2:
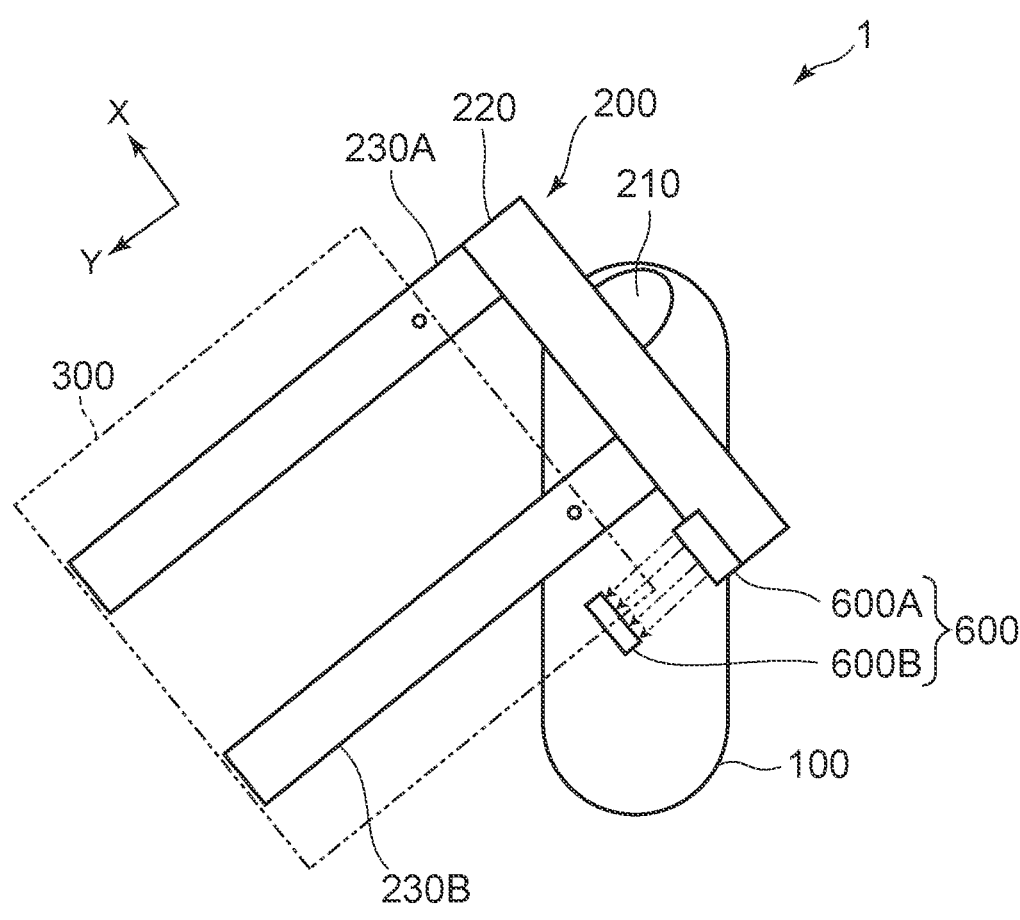
FIG. 2 is a diagram illustrating a top view of a panel transfer device according to one or more embodiments.

FIG. 2 illustrates a panel transfer device 1 according to one or more embodiments. FIG. 2 is particularly illustrative of the position detection of the panel 300 in the X-direction (second position detection) after the end effector 200 has gripped the panel 300. The panel transfer device 1 includes a detector 600. The detector 600 includes an emitter 600A and a receiver 600B that communicates with the emitter 600A. After the end effector 200 grips the panel 300, the end effector 200 rotates to a position where the emitter 600A and the receiver 600B face each other.

The emitter 600A and the receiver 600B communicate and recognize objects between the emitter 600A and the receiver 600B. Communication between the emitter 600A and the receiver 600B includes communication by light. The light, for example, output by the emitter 600A may be detected by the receiver 600B. For example, when the emitter 600A and the receiver 600B are communicating, if an object is present between the emitter 600A and the receiver 600B, communication in that area is interrupted. By detecting the communication interruption, the object between the emitter 600A and the receiver 600B may be recognized. With respect to a predetermined length (width) between the emitter 600A and the receiver 600B, the width to be detected may be determined by the dimensions of the target panel or an error in the position in which the panel is stored in the cassette. The width to be detected may be, for example, 5 mm, 10 mm, 15 mm, 20 mm, 25 mm, 30 mm, 35 mm, 40 mm, 45 mm, 50 mm or more. When the width to be detected is small, installation on the arm 100 or the end effector 200 may be easier, but may not be possible due to errors in the position in which the panel 300 is stored. On the other hand, if the width to be detected is large, errors in the position where the panel 300 is stored may be tolerated, but restrictions on installation on the arm 100 or the end effector 200 may occur. With respect to the location of the emitter 600A and the receiver 600B, the emitter 600A and the receiver 600B may be installed in a position where all or part of the communication between the emitter 600A and the receiver 600B is blocked when the panel 300 is being gripped by the end effector 200. For example, in the panel transfer device 1 shown in FIGS. 1 and 2, the emitter 000A is placed on the end effector 200 and the receiver 600B is placed on the arm 100, but this is not limited. For example, the receiver 600B may be arranged on the end effector 200 and the emitter 600A may be arranged on the arm 100.

When the end effector 200 is rotated to a position where the emitter 600A and the receiver 600B are facing each other, the emitter 600A and the receiver 600B communicate with each other. The panel 300 may recognize the position of the panel 300 by blocking all or part of the communication between the emitter 600A and the receiver 600B. For example, the amount by which the panel 300 interrupts communication between the emitter 600A and the receiver 600B may detect the X-axis displacement of the panel 300. Thus, by detecting the displacement of the panel 300 in the X-axis direction, a second position detection of the panel 300 is performed. The displacement of the panel 300 in the X-axis direction and the displacement of the panel 300 in the Y-axis direction include the angle of inclination of the panel 300 with respect to the end effector 200, the length of inclination of the panel 300 with respect to the end effector 200, or both.

Generally, cassettes for storing multiple panels at predetermined intervals may be used for panel transfer. Panels are removed from the cassette either one by one or multiple by multiple panels for various types of processing. Panels are sometimes stored with a deviation from the predetermined position of the cassette. In such cases, the panel transfer device 1 according to one or more embodiments uses the sensors 231A and 231B to detect the Y-axis inclination angle of the panel 300 as viewed from the forks 230A and 230B. This allows the Y-axis displacement of the panel to be detected. The panel transfer device 1 of one or more embodiments also uses the emitters 600A and the receivers 600B to detect the displacement of the panel 300 in the X-axis direction as viewed from the forks 230A and 230B. From the above, displacement in the X-axis direction and Y-axis direction of the panel 300 as viewed from the forks 230A and 230B may be detected. Based on the detected displacement in the X-axis and Y-axis directions, the controller corrects the position where the panel 300 is placed and controls the end effector 200 to place the panel 300 in the correct position. This improves the accuracy of the alignment of the panel 300.

The controller may detect displacement in the X-axis and Y-axis directions based on the amount of offset from the standard values. If the controller detects a displacement in the X-axis and Y-axis directions that exceeds a predetermined amount, the controller may notify the user with an alarm or the like as an error. The width detected by the emitter 600A and the receiver 600B may be set considering, for example, the displacement in the X-axis and Y-axis directions of the panels stored in the cassette. For example, if the displacement in the X-axis direction is ±2 mm, it may be set to 5 mm or more considering a tolerance of 1 mm. For the panel transfer device for multiple end effectors described below, in the case of a displacement of ±2 mm in the X-axis direction, the value may be set to 10 mm or more.

Figure 3:
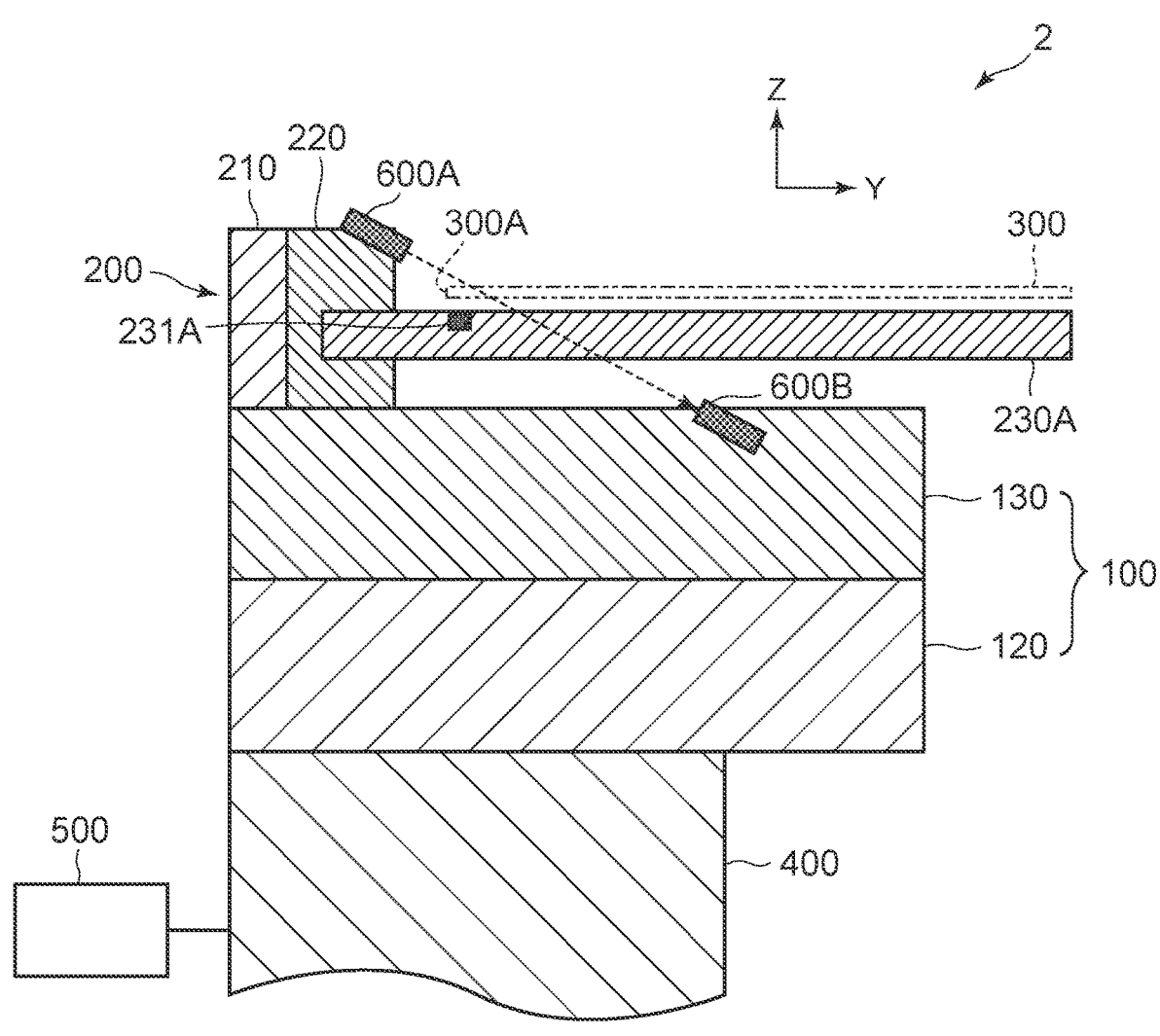
FIG. 3 is a diagram illustrating a cross-sectional view of a panel transfer device according to one or more embodiments.

FIG. 3 is a diagram illustrating a cross-sectional view of a panel transfer device 2 according to one or more embodiments. The panel transfer device 2 detects the front edge 300A of the panel 300 by the sensor 231A when detecting the position of the panel 300. The panel transfer device 2 includes a base 400, an arm 100 rotatably connected to the base 400, and an end effector 200 rotatably connected to the arm 100 and transferring the panel 300. The arm 100 includes a lower link 120 rotatably connected to the base 400 and an upper link 130 rotatably connected to the lower link 120. The end effector 200 is rotatably connected to upper link 130 and transfers the panel 300. FIG. 3 shows the panel transfer device 2 in which the emitter 600A and the receiver 600B communicate and the panel 300 is moved onto the upper link 130 in order for the panel transfer device 2 to detect the position of the panel 300 after the end effector 200 grips the panel 300 using the lower link 120 and upper link 130. The state in which the panel 300 is moved is shown. The base 400 may be fixedly installed on the floor where the panel transfer device 2 is installed. The dimensions of the base 400 are not restricted, but its lower part is omitted. The panel transfer device 2 is particular a horizontal articulated panel transfer device, but it may be implemented other type of panel transfer devices. Various operations of the panel transfer device 2 are controlled by the controller 500. The controller 500 controls the operation of the lower link 120, the upper link 130, and the end effector 200, including rotation. The upper link 130 includes a receiver 600B. The end effector 200 includes the emitter 600A. In FIG. 3, the controller 500 is wired, but is not limited to this, and may be wirelessly connected to the panel transfer device 2 to perform various controls. The controller 500 does not necessarily have to be installed near the panel transfer device 2. For example, the panel transfer device 2 and the controller 500 may be connected to the Internet, and the controller 500 may control the panel transfer device 2 from a remote location. Although the receiver 600B is included in upper link 130, it is not limited to this, and the receiver 600B may be included in lower link 140. In this case, the receiver 600B may be provided at a location where the receiver 600B does not interfere with the upper link 130.

The end effector 200 includes a connector 210 that rotatably connects to upper link 130, a wrist 220 connected to connector 210, and a fork 230A connected to wrist 220. The end effector 200, under the control of the controller 500, for example, retrieves the panel 300 stored in a predetermined position in the cassette using the forks 230A and transfers the panel 300 to the predetermined position. The end effector 200 may include multiple forks. In acquiring the panel 300 stored in place, the forks 230A are advanced above or below the panel 300. In FIG. 3, the forks 230A are not in contact with the panel 300 shown in the imaginary line, but this is not limited to the forks 230A and the panel 300.

The fork 230A includes the sensor 231A. The end effector 200 may also include a fork 230B (not shown) that includes a sensor 231B (not shown). The forks 230A and 230B are advanced above or below the panel 300 in the cassette, and the sensor 231A detects the front edge 300A of the panel 300 to be acquired. The sensor 231A outputs light to detect the front edge 300A of the panel 300 to be acquired. When the front edge 300A of the panel 300 is moved into position, the panel 300 reflects the light output by the sensor 231A. The sensor 231A may detect the front edge 300A of the panel 300 by detecting the reflected light. The sensor 231A uses reflection of light to perform detection, but is not limited to this. For example, a method of detecting the panel 300 using capacitance or a method of detecting the panel 300 using ultrasonic waves may also be used. The sensor 231A also detects the position of the displacement of the panel 300 in the Y-axis direction. For example, multiple sensors 231A and 231B may be installed on the upper link 130 to detect the angle of inclination of the panel 300 in the left and right directions based on the difference in the coordinates of the panel 300. This allows the Y-axis displacement of the panel 300 to be detected. In this way, the panel transfer device 2 performs first position detection by detecting the displacement of the panel 300 in the Y-axis direction. The sensor 231A may be a line sensor in which the sensor elements are arranged in one or more rows to detect the panel 300 in a linear manner. In this case, the sensor 231A may be arranged in a line in a horizontal direction with the direction of entry of the forks 230A and 230B to detect the Y-axis displacement of the panel 300.

After the end effector 200 grips the panel 300, the end effector 200 is rotated to a position where the emitter 600A and receiver 600B are facing each other. The emitter 600A and receiver 600B communicate and recognize objects between the emitter 600A and receiver 600B. Communication between the emitter 600A and the receiver 600B includes communication by light. If an object exists between the emitter 600A and the receiver 600B, communication in the area is interrupted. This allows the object to be recognized. The emitter 600A and the receiver 600B may have a predetermined length (width) to be detected. The width to be detected may be determined by the dimensions of the target panel or the error in the position where the panel is stored.

When the end effector 200 is rotated to move the end effector 200 to a position where the emitter 600A and the receiver 600B are facing each other, the emitter 600A and the receiver 600B communicate with each other. The panel 300 may recognize the position of the panel 300 by blocking all or part of the communication between the emitter 600A and the receiver 600B. For example, the amount by which the panel 300 interrupts communication between the emitter 600A and the receiver 600B may detect the X-axis displacement of the panel 300. By detecting the displacement of the panel 300 in the X-axis direction, a second position detection of the panel 300 is performed.

Since the emitter 600A is positioned at the wrist 220, the risk of interference with the panel 300 or other equipment may be reduced when gripping the panel 300 or transferring the panel 300. The wrist 220 may be positioned higher in the Z-axis direction than the panel 300 when the panel 300 is gripped. The emitter 600A may be positioned higher in the Z-axis direction than the panel 300 when gripping the panel 300.

The controller 500 may include, for example, a computer including a central processing unit (CPU), which reads a computer program stored on a recording medium and, performs various controls for panel transfer in cooperation with the computer program. The computer reads the computer program stored in the recording medium and works with the computer program to perform various controls for panel transferring. The recording medium may include a non-transitory tangible computer-readable storage medium, such as a computer-readable ROM (Read Only Memory). In addition, the recording medium may include tapes, disks, cards, semiconductor memory, programmable logic circuits, etc. may be used. The computer may further be provided with RAM (Random Access Memory) or the like to expand the above program. The above program may be supplied to the above computer via any transmission medium (communication network, broadcast wave, etc.) capable of transmitting the program. The above program may also be realized in the form of a data signal embedded in a carrier wave, which is embodied by electronic transmission.

The order of the first position detection to detect the displacement of the panel 300 in the Y-axis direction and the second position detection to detect the displacement of the panel 300 in the X-axis direction may be whichever performs first. That is, the first position detection detecting the displacement of the panel 300 in the Y-axis direction by the sensor 231A may be followed by the second position detection detecting the displacement of the panel 300 in the X-axis direction by the emitter 600A and the receiver 600B.

As an alternative, a second position detection detecting displacement of the panel 300 in the X-axis direction by the emitter 600A and the receiver 600B may be performed, followed by a first position detection detecting displacement of the panel 300 in the Y-axis direction by the sensor 111.

Figure 4A:
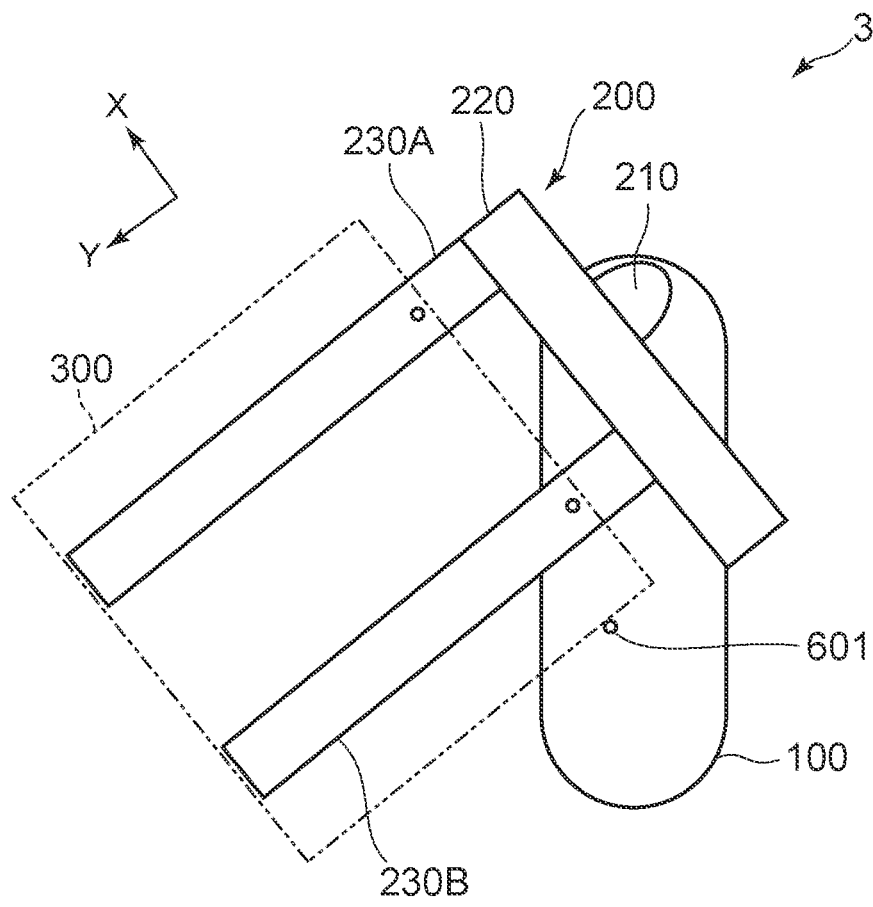
FIG. 4A is a diagram illustrating a top view of a panel transfer device according to one or more embodiments.
Figure 4B:
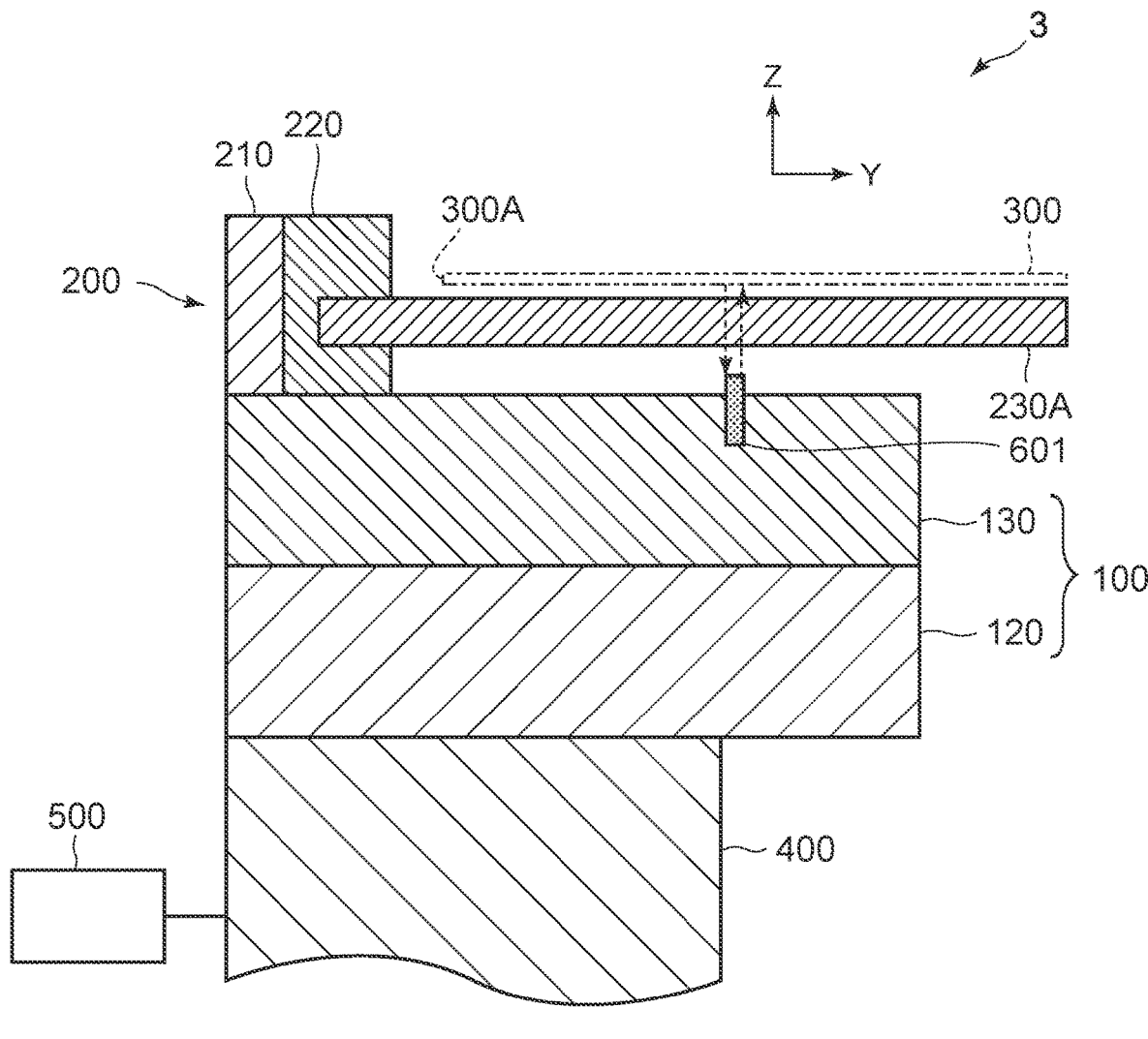
FIG. 4B is a diagram illustrating a cross-sectional view of a panel transfer device according to one or more embodiments.

FIG. 4A is a diagram illustrating a top view of a panel transfer device 3 for one or more embodiments, and FIG. 4B is a diagram illustrating a cross-sectional view of a panel transfer device 3 for one or more embodiments. The panel transfer device 3 includes a base 400, a lower link 120 rotatably connected to the base 400, an upper link 130 rotatably connected to the lower link 120, and an end effector 200 rotatably connected to the upper link 130 and transferring the panel 300. The panel transfer device 3 shown in FIGS. 4A and 4B are diagrams illustrating the panel transfer device 3 moving the panel 300 onto the upper link 130 in order for the panel transfer device 3 to detect the position of the panel 300 after gripping the panel 300 using the end effector 200, lower link 120 and upper link 130. The base 400 may be fixedly installed on the floor where the panel transfer device 3 is installed. The dimensions of the base 400 are not restricted, but its lower part is omitted from the drawings. The panel transfer device 3 is particularly shown as a horizontal articulated panel transfer device, but it may be implemented without the limitation. Various operations of the panel transfer device 3 are controlled by the controller 500. The controller 500 controls the operation of the lower link 120, the upper link 130, and the end effector 200, including rotation. The upper link 130 includes a detector 601. In FIG. 4A, the controller 500 is wired, but it is not limited to this, and may be wirelessly connected to the panel transfer device 3 to perform various controls. The controller 500 does not need to be installed near the panel transfer device 3. For example, the panel transfer device 3 and the controller 500 may be connected to the Internet, and the controller 500 may control the panel transfer device 3 from a remote location via the Internet.

The end effector 200 includes a connector 210 that rotatably connects to upper link 130, a wrist 220 connected to connector 210, and a fork 230A connected to wrist 220. The end effector 200, under the control of the controller 500, retrieves the panel 300 stored at a predetermined position using the forks 230A and transfers the panel 300 to the predetermined position. The end effector 200 may include multiple forks. When acquiring a panel 300 stored in a predetermined position, the forks 230A are advanced above or below the panel 300.

The fork 230A includes a sensor (not shown). The sensor detects the front edge 300A of the acquired panel 300. The sensor also performs first position detection by detecting a displacement of the panel 300 in the Y-axis direction.

After the end effector 200 grips the panel 300, the end effector 200 is rotated to a position where the detector 601 may detect the position of the panel 300. The detector 601 outputs light. The panel 300 reflects the light output by the detector 601. The detector 601 may detect the position of panel 300 by detecting the reflected light. The detector 601 uses the reflection of light to perform detection, but is not limited to this. For example, a method of detecting the position of the panel 300 using capacitance or a method of detecting the position of the panel 300 using ultrasonic waves may also be used. For example, a plurality of detectors 601 may be installed in the upper link to detect the displacement of the panel 300 in the x-direction based on the difference in the coordinates of the panel 300. The detector 601 may have a predetermined length (width) to detect the position of the panel 300. The width to be detected may be determined by the dimensions of the target panel and the error in the position where the panel is stored. In this case, the panel 300 may recognize the position of the panel 300 by blocking all or part of the light output by the detector 601. For example, the amount of light that the panel 300 blocks the light output by the detector 601 may detect the displacement of the panel 300 in the X-axis direction. By detecting the displacement of the panel 300 in the X-axis direction, a second position detection of the panel 300 is performed.

The detector 601 is located on the upper link 130, which reduces the risk of interference with the panel 300 or other equipment when gripping the panel 300 or transferring the panel 300.

The order of the first position detection to detect the displacement of the panel 300 in the Y-axis direction and the second position detection to detect the displacement of the panel 300 in the X-axis direction may be whichever performs first. That is, the first position detection to detect the displacement of the panel 300 in the Y-axis direction by the sensor (not shown) may be performed, followed by the second position detection to detect the displacement of the panel 300 in the X-axis direction by the detector 601. As an alternative, a second position detection detecting the displacement of the panel 300 in the X-axis direction by the detector 601 may be performed, followed by a first position detection detecting the displacement of the panel 300 in the Y-axis direction by the sensor.

Figure 5:
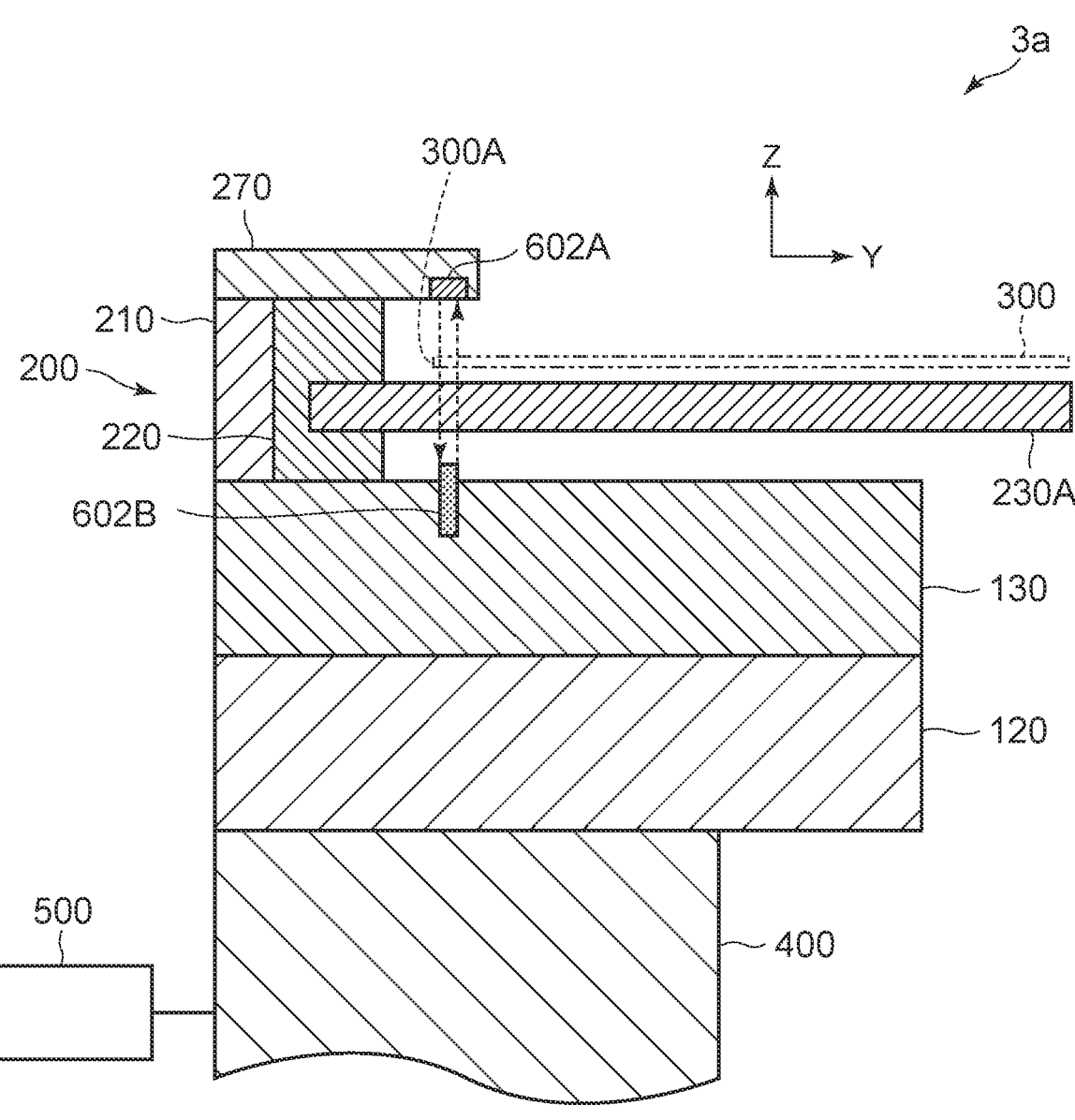
FIG. 5 is a diagram illustrating a cross-sectional view of a panel transfer device according to one or more embodiments.

FIG. 5 is a cross-sectional view of a panel transfer device 3a according to one or more embodiments. The panel transfer device 3a includes a base 400, a lower link 120 rotatably connected to the base 400, an upper link 130 rotatably connected to the lower link 120, and an end effector 200 rotatably connected to the upper link 130 and transferring a panel 300. The panel transfer device 3a in FIG. 5 shows the status that the panel 300 is transferred onto the upper link 130 for detecting the position of the panel 300 by the panel transfer device 3a after gripping the panel 300 using the lower link 120 and upper link 130. The panel transfer device 3a includes an emitter 602A in the detector holder 270 connected to the wrist 220 and a receiver 602B in the upper link 130. The emitter 602A and the receiver 602B detect the position of the gripped panel 300.

The end effector 200 includes a connector 210 rotatably connected to upper link 130, a wrist 220 connected to connector 210, a detector holder 270 connected to wrist 220, an emitter 602A included in detector holder 270, and a 230A, and a fork 230A. Under the control of the controller 500, the end effector 200 retrieves the panel 300 stored at a predetermined position using the forks 230A and transfers the panel 300 to the predetermined position. The end effector 200 may include multiple forks. When acquiring a panel 300 stored in a predetermined position, the forks 230A moves above or below the panel 300.

The upper link 130 includes a sensor (not shown). The sensor detects the front edge 300A of the acquired panel 300. The sensor also performs first position detection by detecting the displacement of the panel 300 in the Y-axis direction. The emitter 602A and the receiver 602B communicate and recognize objects between the emitter 602A and the receiver 602B. Communication between the emitter 602A and the receiver 602B includes communication by light. For example, the light output by the emitter 602A may be detected by the receiver 602B. For example, when the emitter 602A and the receiver 602B are communicating, if an object is present between the emitter 602A and the receiver 602B, communication in that area is interrupted. By detecting the communication interruption, the object between the emitter 602A and the receiver 602B may be recognized. With respect to a predetermined length (width) between the emitter 602A and the receiver 602B, the width to be detected may be determined by the dimensions of the target panel or an error in the position in which the panel is stored in the cassette. The width to be detected may be, for example, 5 mm, 10 mm, 15 mm, 20 mm, 25 mm, 30 mm, 35 mm, 40 mm, 45 mm, 50 mm or more. For example, a plurality of emitters 602A and the receivers 602B may be provided to detect displacement of panel 300 in the x-direction based on the difference in coordinates of panel 300. In this case, the panel 300 may recognize the position of the panel 300 by blocking all or part of the light output by the plurality of emitters 602A and the receivers 602B. For example, the amount by which the panel 300 blocks the light output by the plurality of emitters 602A may detect the displacement of the panel 300 in the X-axis direction. By detecting the displacement of the panel 300 in the X-axis direction, a second position detection of the panel 300 is performed.

Since the emitter 602A is located on upper link 130 and the receiver 602B is located on upper link 130, the risk of interference with panel 300 or other devices may be reduced when gripping panel 300 or transferring panel 300. For example, in the panel transfer device 3a shown in FIG. 5, the emitter 602A is placed on the detector holder 270 and the receiver 602B is placed on the upper link 130, but this is not limited. For example, the receiver 602B may be placed on the detector holder 270 and the emitter 602A may be placed on the upper link 130.

The fork 230A includes a sensor (not shown). The sensor detects the front edge 300A of the acquired panel 300. The sensor also performs first position detection by detecting a displacement of the panel 300 in the Y-axis direction.

After the end effector 200 grips the panel 300, the end effector 200 is rotated to a position where the emitter 602A and the receiver 602B may detect the position of the panel 300. The emitter 602A outputs light. The receiver 602B receives the light output by the emitter 602A. The receiver 602B may detect the position of panel 300 by detecting the received light. The emitter 602A and the receiver 602B use light to detect the position of panel 300, but are not limited to this. For example, a method of detecting the position of the panel 300 using capacitance or a method of detecting the position of the panel 300 using ultrasonic waves may also be used. For example, a plurality of emitters 602A and the receivers 602B may be provided to detect the displacement of the panel 300 in the X direction based on the difference in the coordinates of the panel 300. The emitters 602A and the receivers 602B may have a predetermined length (width) to communicate with each other to detect the position of the panel 300. The width to be detected may be determined by the dimensions of the target panel or the error in the position where the panel is stored. In this case, the panel 300 may block all or part of the light output by the emitter 602A, and the receiver 602B may detect the blockage to recognize the position of the panel 300. For example, the amount by which the panel 300 blocks the light output by the emitter 602A may detect the displacement of the panel 300 in the X-axis direction. By detecting the displacement of the panel 300 in the X-axis direction, a second position detection of the panel 300 is performed.

The emitter 602A is located on the upper link 130, which reduces the risk of interference with panel 300 or other equipment when gripping or transferring panel 300.

The order of the first position detection to detect the displacement of the panel 300 in the Y-axis direction and the second position detection to detect the displacement of the panel 300 in the X-axis direction may be whichever performs first. That is, the first position detection to detect the displacement of the panel 300 in the Y-axis direction by the sensor (not shown) may be performed, followed by the second position detection to detect the displacement of the panel 300 in the X-axis direction by the emitter 602A and the receiver 602B. As an alternative, a second position detection detecting displacement of the panel 300 in the X-axis direction by the emitter 602A and the receiver 602B may be performed, followed by a first position detection detecting displacement of the panel 300 in the Y-axis direction by the sensor.

Figure 6:
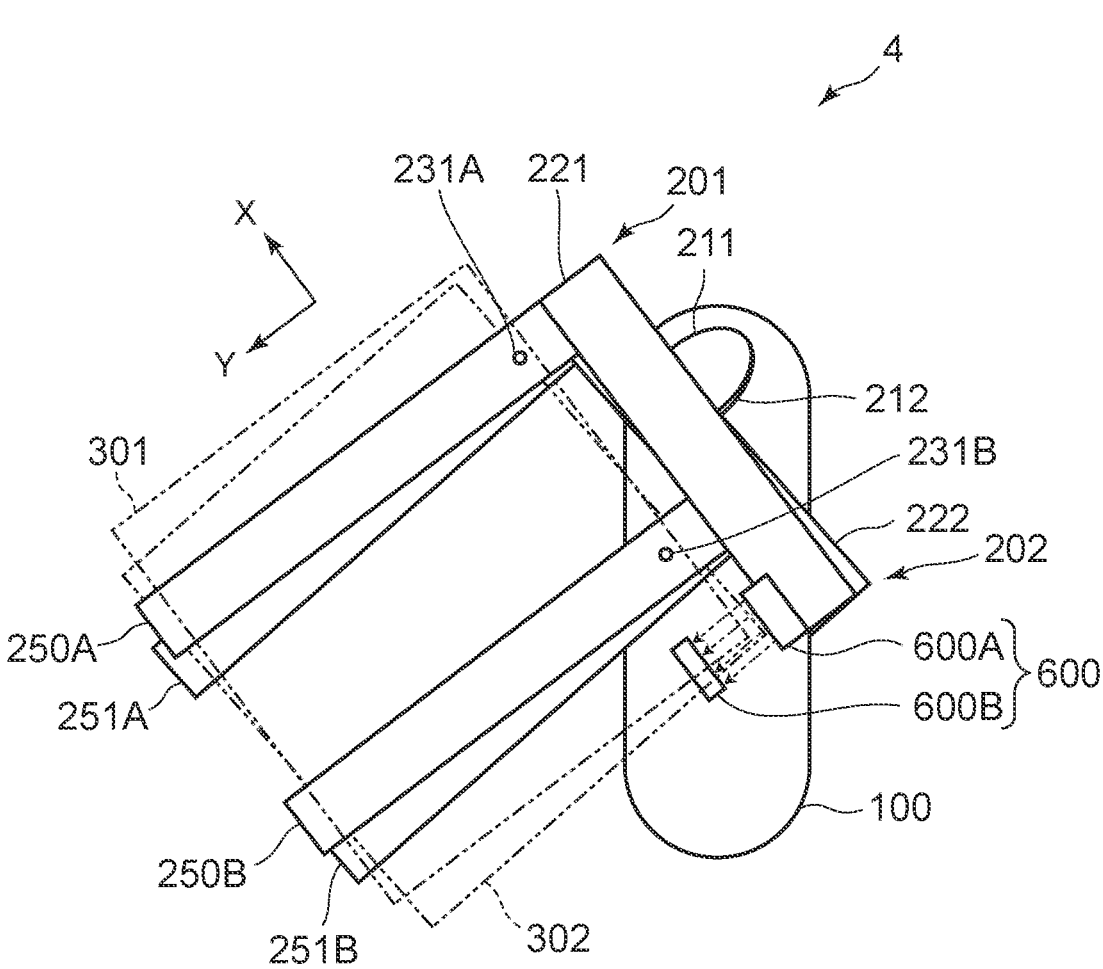
FIG. 6 is a diagram illustrating a top view of a panel transfer device one or more embodiments.

FIG. 6 is a diagram illustrating a panel transfer device 4 according to one or more embodiments. Particularly, FIG. 6 illustrates the second position detection of panels 301 and 302 after a plurality of end effectors (end effectors 201 and end effector 202) have gripped a plurality of panels 301 and 302. The panel transfer device 4 includes the end effector 201 and the end effector 202, each of the end effector 201 and 202 may operate independently. The end effector 201 includes a connector 211 that is rotatably connected to the arm 100, a wrist 221 connected to the connector 211, and a pair of forks 250A and 250B connected to the wrist 221. The end effector 202 includes a connector 212 rotatably connected to arm 100, a wrist portion 222 connected to the connector 212, and a pair of forks 251A and 251B connected to wrist portion 222. The end effector 201 and the end effector 202 are independently rotatable and movable with respect to arm 100. The end effector 201 and the end effector 202 may rotate concentrically by means of connector 211 and connector 212. The end effector 202 may be positioned closer to the arm 100 than the end effector 201. In other words, when the base (not shown) is placed on the floor, the end effector 201 may be positioned above the end effector 202. To detect the Y-axis displacement of panels 301 and 302 as viewed from forks 250A, 250B and forks 251A, 251B, the end effectors 201 and the end effector 202 may each include multiple sensors. This allows each of the multiple panels 301 and 302 to detect displacement in the Y-axis direction. The panel transfer device 4 of one or more embodiments also uses the emitter 600A and the receiver 600B to detect displacement of panels 301 in the X-axis direction as viewed from forks 250A and 250B. Similarly, the panel transfer device 4 uses the emitter 600A and the receiver 600B to detect the X-axis displacement of panel 302 as viewed from forks 251A and 251B. From the above, the displacement of panels 301 and 302 in the X-axis and Y-axis directions as viewed from the end effectors 201 and 202 may be detected. Based on the detected displacement in the X-axis and Y-axis directions, the position where the panel 300 is placed is corrected and the panel 300 is placed in the correct position. This may improve the accuracy of the positioning of the panel 300.

The end effector 201 uses forks 250A and 250B to retrieve panels 301 stored in place under the control of the controller (not shown). The end effector 202 uses forks 251A and 251B to retrieve panels 302 stored at predetermined positions under the control of the controller. The panel transfer device 4 may acquire multiple panels 302 and 301 simultaneously or separately using the end effectors 201 and the end effector 202. After the end effectors 201 and 202 have gripped the panels 301 and 302, the rotational angles of the end effectors 201 and 202 are adjusted as shown in the figure to create a portion where the panel 301 does not overlap the panel 302. The end effector 201 and the end effector 202 are then rotated to the position where the emitter 600A and the receiver 600B on the arm 100 are facing each other.

The emitter 600A and the receiver 600B communicate and recognize panels 301 and 302 between the emitter 600A and the receiver 600B. Communication between the emitter 600A and the receiver 600B includes communication by light. The detection range between the emitter 600A and the receiver 600B may have a predetermined length (width). This allows the location of panels 301 and 302 between emitter 600A and the receiver 600B to be detected by detecting the length (width) of the communication interruption between the emitter 600A and the receiver 600B, rather than just recognizing panels 301 and 302. As shown in FIG. 6, by controlling the rotation of the end effector 201 and the end effector 202, panel 301 does not overlap panel 302. To do this, the controller rotates and moves only one arm of the end effector 201 and the end effector 202, which rotate and move in concentric circles, by a small amount. This creates a portion of the panel 301 that does not overlap the panel 302. The portion where panel 301 does not overlap panel 302 is made so that the emitter 600A and the receiver 600B may detect the displacement of each of panel 301 from panel 302. Specifically, of the end effectors 201 and 202 that rotate and move in concentric circles, the amount of rotation to rotate and move only the end effector 202 should be enough to allow the emitter 600A and the receiver 600B to detect the displacement of each of the panels 301 from the panel 302. Because there are areas where panel 301 does not overlap panel 302, there will be differences when the emitter 600A and the receiver 600B communicate. For example, when the emitter 600A and the receiver 600B detect panels through communication by light, the detector on the receiving side detects the area where panel 301 overlaps panel 302, the area where panel 301 does not overlap panel 302, and the area where panel 301 and panel 302 are not present. The light intensity differs. By detecting this difference, the emitter 600A and the receiver 600B may detect the displacement of panel 301 and panel 302 in the X-axis direction.

Figure 7:
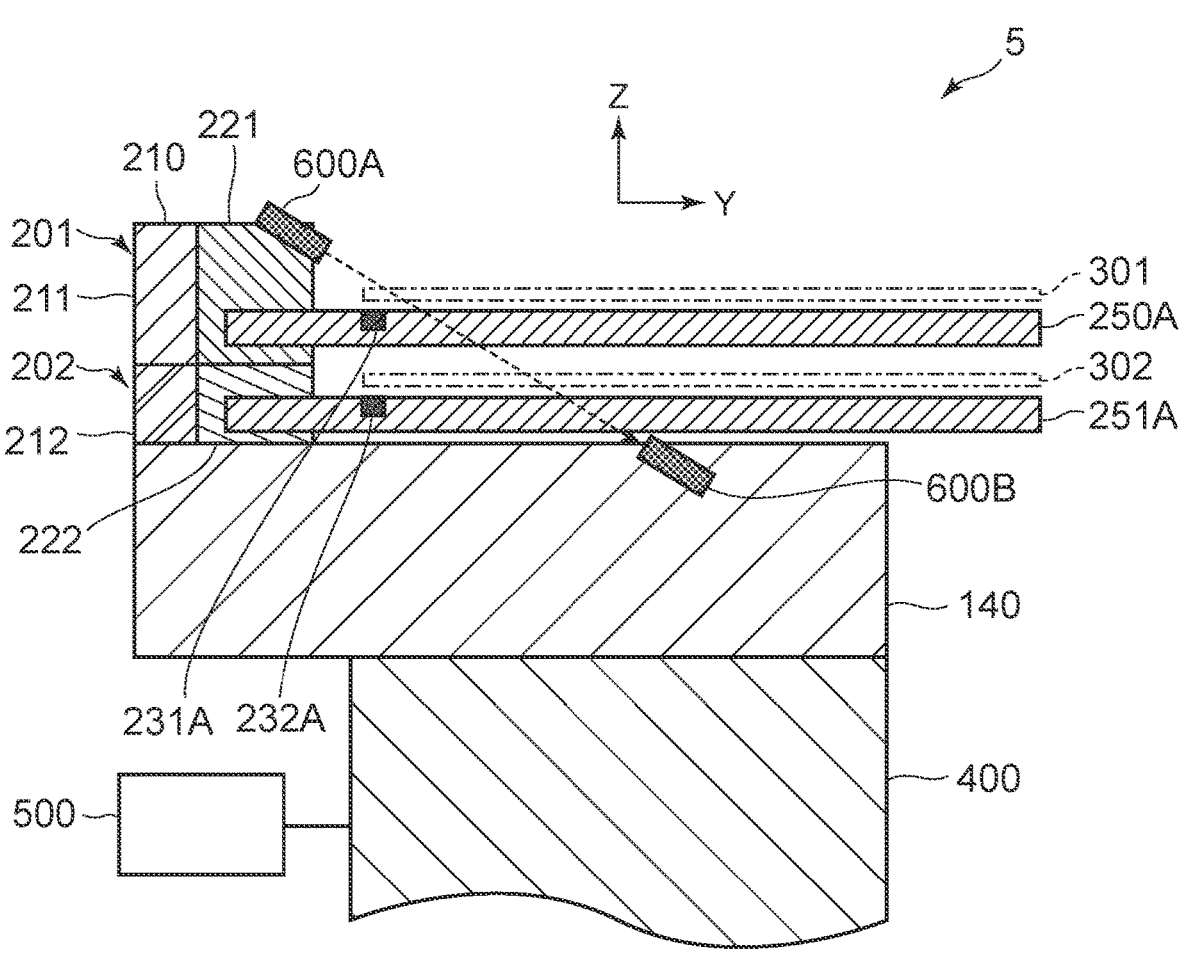
FIG. 7 is a diagram illustrating a cross-sectional view of a panel transfer device according to one or more embodiments.

FIG. 7 is a cross-sectional view of a panel transfer device 5 according to one or more embodiments. The panel transfer device 5 includes a base 400, a link 140 rotatably connected to the base 400, and a plurality of the end effectors 201 and 202 rotatably connected to the link 140 and transferring panels 301 and 302. The link 140 includes a receiver 600B. The panel transfer device 5 includes a plurality of the end effectors 201 and 202. To detect the Y-axis displacement of the panel 301 as viewed from the forks 250A and 250B, a sensor 231A is provided on the end effector 201. In addition, sensor 232A is provided in the end effector 202 to detect the Y-axis displacement of panel 302 as viewed from 251A, 251B. The configuration of the other panel transfer devices 5 and the gripping operation of the panels 301 and 302 may be the same as the various panel transfer devices described above. The gripping of multiple panels and the detection of displacement of multiple panels may be the same as in the various panel transfer devices described above.

Figures 8A, 8B:
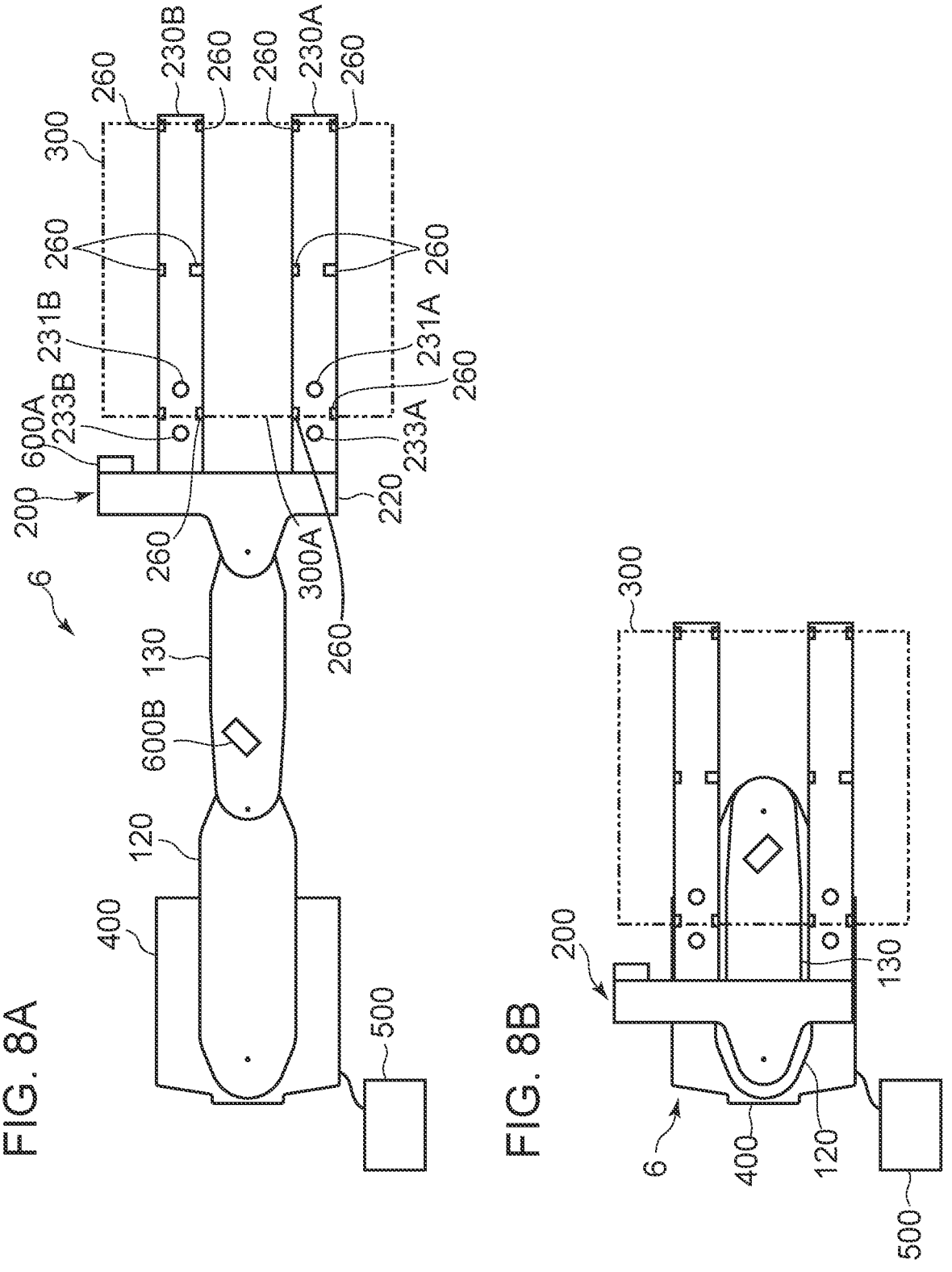
FIGS. 8A and 8B are diagrams illustrating top views of a panel transfer device according to one or more embodiments.

FIGS. 8A and 8B show a panel transfer device 6 in one or more embodiments. The panel transfer device 6 includes a lower link 120 rotatably connected to a base 400, an upper link 130 rotatably connected to the lower link 120, and an end effector 200 rotatably connected to the upper link 130 and transferring the panel 300. The panel transfer device 6 is particularly a horizontally articulated panel transfer device. Various operations of the panel transfer device 6 are controlled by the controller 500. The controller 500 controls the operation of the lower link 120, the upper link 130, and the end effector 200, including rotation of the end effector 200.

The first end of the lower link 120 is rotatably connected to the base 400. The first end of the upper link 130 is rotatably connected to the second end of the lower link 120. The end effector 200 is rotatably connected to the second end of the upper link 130. Other configurations may be similar to the panel transfer device 1 shown in FIG. 1, for example.

The end effector 200 includes a wrist 220 that rotatably connects to upper link 130 and forks 230A and 230B connected to wrist 220. The end effector 200, under the control of the controller 500, retrieves the panel 300 from a predetermined position using the forks 230A and 230B and transfers it to a predetermined position. The fork 230A includes sensor 231A. The fork 230B also includes sensor 231B. The configuration and operation of the sensors 231A and 231B, may be the same as that of the panel transfer device 1 shown in FIG. 1, for example.

The panel transfer device 6 shown in FIGS. 8A and 8B includes sensors 233A and 233B. Under the control of the controller 500, the panel 300 is retrieved from a predetermined position using forks 230A and 230B, and the panel 300 is transferred to the predetermined position. The fork 230A includes the sensor 231A and the sensor 233A. The fork 230B also includes the sensor 231B and the sensor 233B. The sensors 233A and 233B detect the front edge 300A of the panel 300. In retrieving the panel 300 from a predetermined position, the forks 230A and 230B are advanced above or below the panel 300. In doing so, the panel 300 passes through the sensors 231A and 231B and further approaches the sensors 233A and 233B. The sensors 233A and 233B detect the front edge 300A of the panel 300 to be acquired. When the sensors 233A and 233B detect the front edge 300A of the panel 300 to be acquired, they recognize that the forks 230A and 230B have been advanced to the predetermined position. The sensors 231A and 231B detect the coordinates of the panel 300 respectively, and based on the difference between these detected coordinates, detect the vertical tilt angle of the panel 300. This detects the displacement of the panel 300 in the Y-axis direction, thereby performing the first position detection of the panel 300.

The panel transfer device 6 includes a plurality of suction units 260. The plurality of suction units 260 are located on forks 230A and 230B. As shown in FIG. 8A, the plurality of suction units 260 are located at two locations, a pair each at the tip, center, and base of forks 230A and 230B. The suction units 260 at the root are located between the sensors 231A and 231B on forks 230A and 230B and the sensors 233A and 233B. The panel transfer device 6 brings the plurality of suction units 260 located on the forks 230A and 230B and the panel 300 into proximity or contact and applies negative pressure to cause the suction units 260 to be attracted to the panel 300. As a result, the end effector 200 grips the panel 300 and transfers it to a predetermined position. When bringing the plurality of suction units 260 into proximity or contact with the panel 300, the plurality of suction units 260 are brought into proximity or contact with the panel 300 from the top or bottom surface.

FIG. 8B is a diagram illustrating a panel transfer device 6 according to one or more embodiments. FIG. 8B particularly shows the lower link 120, upper link 130, and the end effector 200 moved onto the base 400. Controller 500 controls the operation of lower link 120, upper link 130, and the end effector 200, and controls the rotation of lower link 120, upper link 130, and the end effector 200 to move them to the top of base 400.

Figure 9:
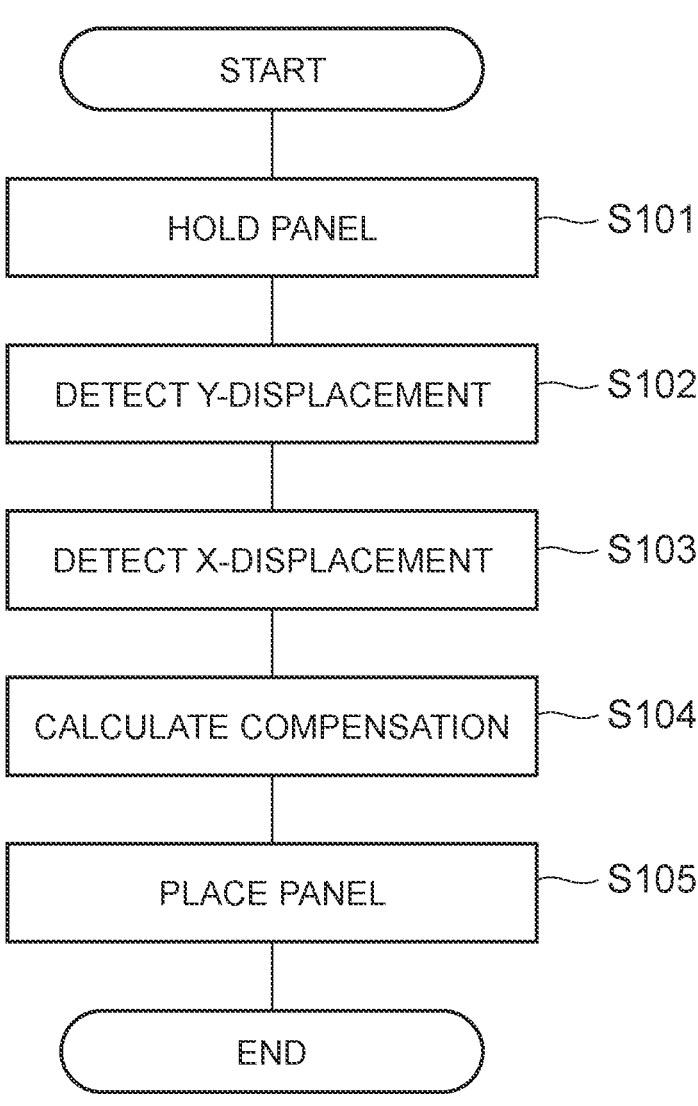
FIG. 9 is a flowchart illustrating a panel transfer method according to one or more embodiments.

FIG. 9 is a flowchart illustrating a panel transfer method according to one or more embodiments. The panel transfer device 1 shown in FIGS. 1 and 2 is used to explain the method. First, the panel is gripped (step S101). The controller 500 controls the forks 230A and 230B to move above or below the panel 300. The panel 300 approaches the sensors 231A and 231B. The sensors 231A and 231B recognize that forks 230A and 230B have been moved into a position to grip the panel 300 when the sensors 231A and 231B detect the front edge 300A of the panel 300. When the forks 230A and 230B are recognized as having advanced the panel 300 to a predetermined position, the forks 230A and 230B stop advancing. The gripping operation of the panel 300 is then performed. Next, the displacement of the panel 300 in the Y-axis direction is detected (step S102). After gripping the panel 300, the sensors 231A and 231B detect the coordinates of the panel 300 respectively, and based on the difference of these detected coordinates, the vertical tilt angle of the panel 300 is detected. This detects the displacement of the panel 300 in the Y-axis direction, thereby performing the first position detection of the panel 300. The first position detection may be performed after the panel 300 is gripped, either with the panel 300 stopped immediately after the panel 300 is gripped, or with the panel 300 being transferred to a predetermined position.

Next, displacement in the X-axis direction is detected (step S103). When the end effector 200 is rotated and the end effector 200 moves to a position where the emitter 600A and the receiver 600B are facing each other, the emitter 600A and the receiver 600B communicate with each other. The panel 300 may recognize the position of the panel 300 by blocking all or part of the communication between the emitter 600A and the receiver 600B. For example, the amount by which the panel 300 interrupts communication between the emitter 600A and the receiver 600B may detect the X-axis displacement of the panel 300. Thus, by detecting the displacement of the panel 300 in the X-axis direction, a second position detection of the panel 300 is performed.

For example, in the case of a panel transfer device including a plurality of the end effectors 201 and 202 shown in FIGS. 6 and 7, by adjusting the angle of rotation between the end effector 201 and the end effector 202, as shown in FIG. 6, a portion of panel 301 does not overlap panel 302 The end effectors 201 and 202 are then rotated to the position where the emitter 600A and the receiver 600B on the arm 100 are facing each other. After rotating the end effector 201 and the end effector 202 to the position where the emitter 600A and the receiver 6008 on the arm 100 are facing each other, the angle of rotation of the end effector 201 and the end effector 202 is adjusted so that the panel 301 is facing the panel 302 A portion of the panel may be made that does not overlap. This allows the emitter 600A and the receiver 600B to detect the displacement of panels 301 and 302 in the x-direction by detecting panels 301 and 302. This allows for a second position detection of panels 301 and 302.

Another embodiment of detecting displacement of multiple panels in the X-direction is described with reference to FIG. 6. First, the end effector 201 is rotated to move the end effector 201 to a position where the emitter 600A and the receiver 600B are facing each other. This allows the emitter 600A and the receiver 6008 to communicate. The panel 301 interrupts all or part of the communication between the emitter 600A and the receiver 600B, so that the emitter 600A and the receiver 600B are aware of the position of the panel 301. For example, the amount by which the panel 301 interrupts communication with the emitter 600A and the receiver 6008 may detect the X-axis displacement of the panel 301. Next, the end effector 202 is rotated to move the end effector 202 to a position where the emitter 600A and the receiver 600B may recognize the position of the panel 302. The panel 302 interrupts all or part of the communication between the emitter 600A and the receiver 600B, so that the emitter 600A and the receiver 600B recognize the position of the panel 302. For example, the amount by which panel 302 interrupts communication between the emitter 600A and the receiver 600B may detect the displacement of panel 302 in the x-axis direction. Thus, by detecting the displacement of panels 301 and 302 in the X-axis direction, a second position detection of panels 301 and 302 is performed.

A further embodiment of detecting displacement of multiple panels in the X-direction is described with reference to FIG. 6. First, the end effector 201 is rotated to move the end effector 201 to a position where the emitter 600A and the receiver 6008 are facing each other. This allows the emitter 600A and the receiver 600B to communicate. The panel 301 interrupts all or part of the communication between the emitter 600A and the receiver 600B, so that the emitter 600A and the receiver 600B are aware of the position of the panel 301. For example, the amount by which the panel 301 interrupts communication with the emitter 600A and the receiver 600B may detect the X-axis displacement of the panel 301. Next, the end effector 202 is rotated to a position where it is completely overlapped in implementation with the end effector 201. At this time, the end effector 202 may be rotated by an angle substantially equal to the angle of rotation of the end effector 201, receiving the angle of rotation of the end effector 201 detected by the end effector rotation controller (not shown) that controls the angle of rotation of the end effector 201. In this case, if the emitter 600A and the receiver 600B may detect the panel 302 placed on the end effector 202, i.e., if the X-axis displacement of the panel 301 and the panel 302 is different. On the other hand, if the emitter 600A and the receiver 600B may not detect the panel 302 placed on the end effector 202, i.e., the X-axis displacement between the panel 301 and the panel 302 is equal, or the panel 302 is misaligned in the X-axis direction that may not be detected, the end effector Based on the control of the rotation controller, the end effector 202 moves a predetermined angle. After that, the emitter 600A and the receiver 600B again detect the panel 302 placed on the end effector 202. At this time, if the emitters 600A and the receivers 600B may detect the panel 302 placed on the end effector 202, that is, if the X-axis displacement of the panel 301 and the panel 302 is different, the emitter 600A and the receiver 600B detect the X-axis displacement of panel 302. On the other hand, if the emitter 600A and the receiver 600B may not detect panel 302 placed on the end effector 202, the end effector 202 is further moved by a predetermined angle based on the control of the end effector rotation controller. In this way, the end effector 202 is rotated until the panel 302 may be detected, and the displacement of the panel 302 in the X-axis direction is detected.

In the embodiment, the displacement in the X-axis direction of a panel 301 placed on the upper end effector 201 of the plurality of end effectors is detected, followed by the displacement in the X-axis direction of a panel 302 placed on the lower end effector 202, but not limited to the order. For example, the displacement in the X-axis direction of the panel 302 placed on the end effector 202 provided at the bottom may be detected first, and then the displacement in the X-axis direction of the panel 301 placed on the end effector 201 provided at the top may be detected.

Next, based on the displacement of the panel 300 in the Y-axis direction detected in step S102 and the displacement of the panel 300 in the X-axis direction detected in step S103, a correction amount (compensation) is calculated (step S104). The controller calculates the amount of correction in the Y-axis and K-axis directions when placing the panel 300 in the next step based on the displacement in the Y-axis direction and X-axis direction of the gripped panel 300. For detecting the displacement of the controller in the X-axis and Y-axis directions, standard values may be defined, the amount of offset from the standard values may be detected, and the displacement in the X-axis and Y-axis directions may be calculated from the offset amount. Next, based on the correction amount calculated in step S104, the gripped panel 300 is placed at a predetermined position (step S105).

Figure 10:
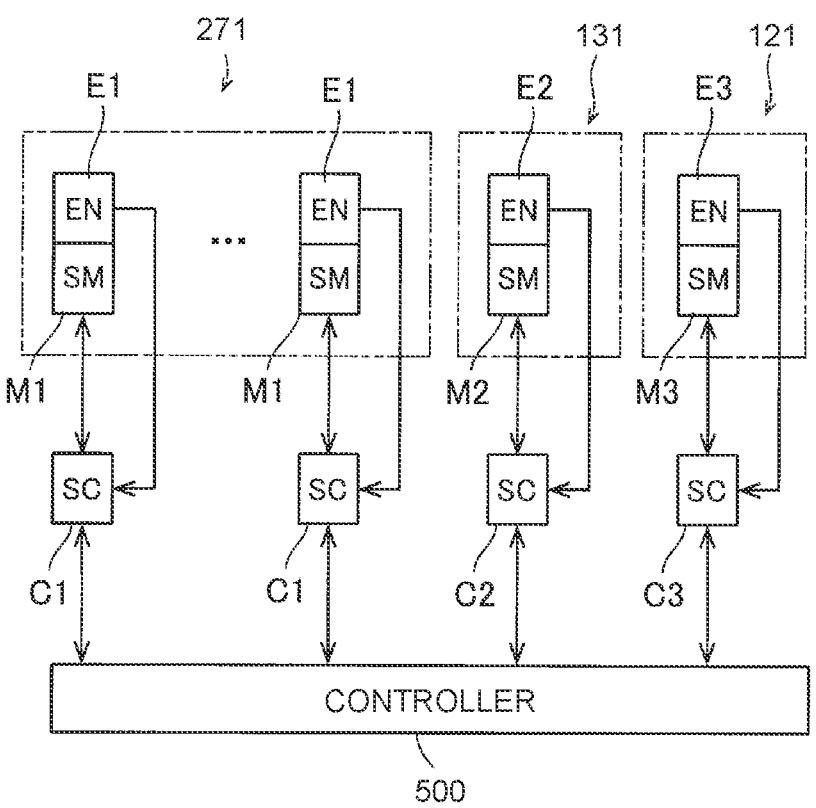
FIG. 10 is a block diagram of controlling arms, links, end effectors, etc. according to one or more embodiments.

FIG. 10 is a block diagram illustrating the rotational control of arms, links, and the end effectors, etc. according to one or more embodiments. The panel transfer device 6 shown in FIGS. 8A and 8B is used in the explanation. As shown in FIG. 10, the end effector 200 is rotatably connected to upper link 130. The end effector 200 includes an end effector rotation controller 271 that controls the rotation of the end effector 200. The end effector rotation controller 271 includes a servo motor M1 that generates rotational power for the end effector 200, an encoder E1, a reduction gear (not shown), and a servo controller C1. The encoder E1 detects the angle of rotation of the servo motor M1. The decelerator increases the torque by decelerating the rotation of the servomotor M1. The servo controller C1 controls the rotation of servo motor M1. The servo controller C1 is electrically connected to encoder E1 and receives the rotation angle of servo motor M1. Based on the rotation angle of servo motor M1 detected by encoder E1, the rotation angle of the end effector 200 is detected. The servo controller C1 sends the rotation angle of servo motor M1 and other information to controller 500. The controller 500 sends the following operation instructions to the servo controller C1.

For example, in the case of having multiple end effectors 201 and 202, as in the panel transfer device 4 shown in FIG. 6, the rotation controller 271 may include multiple servo motors M1, multiple encoders E1, multiple reduction gears, and multiple servo controls C1 to control the rotation of the end effectors 201 and 202, respectively. The rotation control may be performed for each of the end effectors 201 and 202.

The upper link 130 includes an upper link rotation controller 131 that controls the rotation of the upper link 130. The upper link rotation controller 131 includes a servo motor M2 that generates rotational power for the upper link 130, an encoder E2, a reduction gear (not shown), and a servo controller C2. The encoder E2 detects the angle of rotation of the servo motor M2. The decelerator increases the torque by decelerating the rotation of servo motor M2. The servo controller C2 controls servo motor M2. The servo controller C2 is electrically connected to encoder E2 and detects the rotation angle of upper link 130 based on the rotation angle of servo motor M2. The servo controller C2 sends the rotation angle of servo motor M2 and other information to controller 500. The controller 500 sends the following operation instructions to the servo controller C2.

The lower link 120 includes a lower link rotation controller 121 that controls the rotation of the lower link 120. The lower link rotation controller 121 includes a servo motor M3 that generates rotational power for the lower link 120, an encoder E3, a reduction gear (not shown), and a servo controller C3. The encoder E3 detects the angle of rotation of the servo motor M3. The decelerator increases the torque by decelerating the rotation of servo motor M3. The servo controller C3 controls servo motor M3. The servo controller C3 is electrically connected to encoder E3 and detects the rotation angle of lower link 120 based on the rotation angle of servo motor M3. The servo controller C3 sends the rotation angle of servo motor M3 and other information to controller 500. The controller 500 sends the following operation instructions to the servo controller C3.

Thus, according to the panel transfer method of one or more embodiments, the panel transfer method detects the displacement of the panel in the X-axis and Y-axis directions caused when the panel is gripped, corrects the position where the panel is placed, and places the panel in the correct position based on the correction. This improves the accuracy of the alignment of the placed panel.

One or more of the embodiments described above herein may be combined with one another to the extent feasible within the scope of the intended embodiments. The embodiments described above should be considered exemplary in all respects and not limiting. The illustrated and described embodiments may be extended to encompass other embodiments in addition to those specifically described without departing from the technical scope. The technical scope should be determined in light of the specification, including equivalents, and not solely by the foregoing description. Thus, all configurations that contain technical scope and equivalents are intended to be included in the technical scope.

The invention claimed is:

1. A panel transfer device comprising:
a base;
an arm rotatably connected to the base, which comprises a first detector;
an end effector connected to the arm, comprising:
   a connector rotatably connected to the arm;
   a wrist connected to the connector, comprising a second detector; and
   a pair of forks connected to the wrist, comprising a sensor, wherein
in response to the end effector gripping the panel, the sensor detects displacement of the panel in a first direction at the end effector gripping the panel,
the end effector rotates to a position where the first and second detectors face each other,
the first and second detectors communicate to detect displacement of the panel in a second direction, and
the panel transfer device calculates a correction amount based on the detected displacement of the panel in the first direction and in the second direction, and places the panel based on the correction amount.

2. The panel transfer device according to claim 1, wherein the first and second detectors communicate with a predetermined width to detect displacement of the panel in the second direction.

3. The panel transfer device according to claim 2, wherein the first and second detectors recognize the panel by detecting an interruption in communication between the first and second detectors.

4. The panel transfer device according to claim 1, wherein the first detector is positioned lower than the panel.

5. The panel transfer device according to claim 1, wherein the second detector is positioned higher than the panel.

6. The panel transfer device according to claim 1, further comprising:

a second end effector connected to the arm and gripping a second panel comprising:
a second connector rotatably connected to the arm;
a second wrist connected to the second connector; and
a pair of second forks connected to the second wrist, wherein
a second sensor detect a displacement of the second panel in the first direction at the second end effector gripping the second panel,
in response to the first detector facing to the second detector by rotation, the second end effector moves the second panel to a position that creates a portion of the second panel that does not overlap the panel, and the first and second detectors detect displacement of the second panel in the second direction,
the first and second detectors communicate to detect the displacement of the second panel in the second direction, and
the panel transfer device calculates a second correction amount based on the detected displacement of the second panel in the first and second directions, and places the second panel based on the second correction amount.

7. A panel transfer device comprising:
a base;
an arm rotatably connected to the base, which comprises a detector;
an end effector connected to the arm, comprising:
a connector rotatably connected to the arm;
a wrist connected to the connector; and
a first pair of forks connected to the wrist and comprising a first pair of sensors respectively provided on the first pair of forks, and a second pair of forks connected to the wrist and comprising a second pair of sensors respectively provided on the second pair of forks, wherein
the first pair of sensors are configured, in a state where the end effector grips a first panel, to detect displacement of the first panel in a first direction with respect to the end effector gripping the first panel,
the second pair of sensors are configured, in a state in which the end effector grips a second panel, to detect displacement of the second panel in the first direction with respect to the end effector gripping the second panel,
the end effector is configured to move at least one of the first and second panels to a position that creates a portion of the second panel that does not overlap the first panel, to detect by the detector displacement of the first and second panels in a second direction with respect to the end effector gripping the first and second panels, and
the panel transfer device is configured to calculate a correction amount based on the detected displacement of the panel in the first direction and in the second direction, and places the panel based on the correction amount.

8. A method of transferring a panel comprising:
gripping a panel by an end effector;
detecting displacement of the gripped panel in a first direction with respect to the end effector;
moving the end effector to a position in which a first detector and a second detector face each other;
detecting displacement of the gripped panel in a second direction with respect to the end effector, in a state in which the first detector and the second detector face each other;

calculating correction amount based on the detected displacement of the gripped panel in the first and second directions; and placing the gripped panel based on the correction amount.

9. A method of transferring a panel comprising:

gripping a panel;

detecting displacement of the panel in a first direction of the griped panel;

moving the gripped panel to a position to detect displacement of the panel in a second direction;

calculating correction amount on the detected displacement of the panel in the first and second directions; and placing the gripped panel based on the correction amount, wherein the gripping the panel comprising gripping a first and a second panels, the detecting the displacement of the panel in the first direction comprises detecting the displacement of each of the first and second panels in the first direction, the moving the gripped panel to the position comprises moving the second panel to a position that creates a portion of the second panel that does not overlap the first panel and the displacement of the first and second panels in the second direction is detected, the detecting the displacement of the panel in the second direction comprises detecting the displacement of the first panel in the second direction and the displacement of the second panel in the second direction based on the portion of the second panel that does not overlap with the first panel.

\* \* \* \* \*